US010537098B2

(12) United States Patent
Matsumura (10) Patent No.: US 10,537,098 B2
(45) Date of Patent: Jan. 21, 2020

(54) FREEZING BAG CONTAINER

(71) Applicant: TERUMO KABUSHIKI KAISHA, Shibuya-ku, Tokyo (JP)

(72) Inventor: Masaki Matsumura, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 56 days.

(21) Appl. No.: 15/712,518

(22) Filed: Sep. 22, 2017

(65) Prior Publication Data

US 2018/0007890 A1    Jan. 11, 2018

Related U.S. Application Data

(63) Continuation of application No. PCT/JP2016/057339, filed on Mar. 9, 2016.

(30) Foreign Application Priority Data

Mar. 24, 2015 (JP) ................................. 2015-061285

(51) Int. Cl.
  *A01N 1/02*   (2006.01)
  *B65D 77/06*  (2006.01)
  (Continued)

(52) U.S. Cl.
  CPC ............. *A01N 1/0252* (2013.01); *A01N 1/02* (2013.01); *A01N 1/0263* (2013.01);
  (Continued)

(58) Field of Classification Search
  CPC ...... A01N 1/0252; A01N 1/02; A01N 1/0263; A01N 1/0268; B65D 77/04; B65D 77/06;
  (Continued)

(56) References Cited

U.S. PATENT DOCUMENTS 1,987,764 A * 1/1935 Walker ..................... B65D 7/12
                                                          220/612
3,810,367 A * 5/1974 Peterson ................... F25D 3/00
                                                          220/771
(Continued)

FOREIGN PATENT DOCUMENTS

JP    51-106616 U    8/1976
JP    59-170163 U    11/1984
(Continued)

OTHER PUBLICATIONS

The extended European Search Report dated Oct. 5, 2018, by the European Patent Office in corresponding European Patent Application No. 16768423.2-1124. (9 pages).
(Continued)

*Primary Examiner* — Melvin Jones
(74) *Attorney, Agent, or Firm* — Buchanan Ingersoll & Rooney PC (57) ABSTRACT

A container for containing a freezing bag filled with biological tissue and for cooling and warming the freezing bag. The container includes a main body possessing an inner surface, a first side surface and a second side surface positioned opposite the first side surface. The main body is substantially rectangular parallelepiped shaped. The container includes at least one opening in at least one of the first side surface and the second side surface of the container, and at least two ridges spaced apart from one another on the inner surface of the container to create an air gap between the spaced apart ridges, the inner surface of the container and the outer surface of the freezing bag.

15 Claims, 3 Drawing Sheets

(51) Int. Cl.
  *B65D 81/18* (2006.01)
  *B65D 81/38* (2006.01)
  *C12M 1/00* (2006.01)
  *C12M 3/00* (2006.01)
  *B65D 77/04* (2006.01)

(52) U.S. Cl.
  CPC ........... *A01N 1/0268* (2013.01); *B65D 77/04* (2013.01); *B65D 77/06* (2013.01); *B65D 81/18* (2013.01); *B65D 81/38* (2013.01); *B65D 81/3825* (2013.01); *C12M 1/00* (2013.01); *C12M 3/00* (2013.01)

(58) Field of Classification Search
  CPC .... B65D 81/18; B65D 81/38; B65D 81/3825; C12M 1/00; C12M 3/00; F25D 11/003; F25D 3/06; F25D 11/006
  See application file for complete search history.

(56) References Cited

U.S. PATENT DOCUMENTS

| | | | |
|---|---|---|---|
| 3,952,536 A | 4/1976 | Faust et al. | |
| 4,145,895 A * | 3/1979 | Hjertstrand | F25D 3/00 165/47 |
| 4,502,295 A * | 3/1985 | Toledo-Pereyra | A01N 1/02 62/306 |
| 4,630,448 A * | 12/1986 | Bilstad | B65D 81/18 435/2 |
| 4,869,398 A * | 9/1989 | Colvin | A61J 1/1462 222/83 |
| 5,103,651 A * | 4/1992 | Coelho | A01N 1/02 220/592.1 |
| 5,168,712 A * | 12/1992 | Coelho | A23L 3/36 62/373 |
| 5,454,478 A * | 10/1995 | Everson | A45C 13/02 220/23.83 |
| 8,011,171 B2 * | 9/2011 | Repkin | B65B 31/00 220/23.83 |
| 2014/0144800 A1 | 5/2014 | Delorme et al. | |
| 2015/0068232 A1 | 3/2015 | Petrov | |

FOREIGN PATENT DOCUMENTS

| | | |
|---|---|---|
| JP | 7-026375 U | 5/1995 |
| JP | 2000-140069 A | 5/2000 |
| JP | 2002-095708 A | 4/2002 |
| JP | 2002-253206 A | 9/2002 |
| JP | 2003-205016 A | 7/2003 |
| JP | 2003-267471 A | 9/2003 |
| JP | 2004-121669 A | 4/2004 |
| JP | 2014-124234 A | 7/2014 |
| WO | 2009/086136 A2 | 7/2009 |
| WO | 2014/099515 A1 | 6/2014 |

OTHER PUBLICATIONS

International Search Report (PCT/ISA/210) dated Jun. 7, 2016, by the Japanese Patent Office as the International Searching Authority for International Application No. PCT/JP2016/057339.
Written Opinion (PCT/ISA/237) dated Jun. 7, 2016, by the Japanese Patent Office as the International Searching Authority for International Application No. PCT/JP2016/057339.
Office Action (Notice of Reasons for Refusal) dated Nov. 6, 2019, by the Japanese Patent Office in corresponding Japanese Patent Application No. 2017-508192 and an English Translation of the Office Action. (12 pages).

* cited by examiner

FREEZING BAG CONTAINER

CROSS-REFERENCES TO RELATED APPLICATIONS

This application is a continuation of International Application No. PCT/JP2016/057339 filed on Mar. 9, 2016, and claims priority to Japanese Patent Application No. 2015-061285 filed on Mar. 24, 2015, the entire content of both of which is incorporated herein by reference.

TECHNICAL FIELD

The present invention generally relates to a freezing bag container.

BACKGROUND ART

When preserving biological tissue such as biological cells for a relatively long time, the biological tissue is filled into a freezing bag and is cryopreserved by immersing the freezing bag filled with the biological tissue in liquid nitrogen. The freezing bag includes a bag main body which is formed in a bag shape by fusing a plastic film or films. The bag main body is equipped with a filling port and a discharge port. The biological tissue is suspended in a cryopreservation solution or the like, and the suspension is filled into (i.e., introduced into) the bag main body through the filling port to cryopreserve the biological tissue. At the time of using the biological tissue, the freezing bag preserved in liquid nitrogen is taken out and thawed, and the biological tissue is taken out via the discharge port to be used. Japanese Patent Application No. 2003-205016 discloses an example of this process to extract, thaw and use the biological tissue.

Cells may be damaged if biological tissue is frozen by abruptly immersing the biological tissue in liquid nitrogen. Japanese Patent Application No. 2003-267471 thus explains that it is preferable to freeze the biological tissue by cooling it down to −80° C. at a rate of approximately 1° C./minute to 5° C./minute by use of a programmable freezer or the like. On the other hand, at the time of thawing the frozen biological tissue, a method of warming the frozen biological tissue by immersing it in hot water at 37° C. to achieve rapid thawing or a similar method is generally adopted for reducing damage to the cells, as described in Japanese Patent Application No. 2002-253206.

The freezing bag may be broken by mistake by the operator at the time of cooling, freezing, preservation, warming, thawing or the like because the freezing bag is produced using a fragile blank material such as plastic film. In addition, the freezing bags are immersed in liquid nitrogen and frozen in a mutually adhered state and, therefore, it is difficult to take the freezing bag out of liquid nitrogen. In order to solve such a problem, bags and containers for protecting the freezing bags have been developed.

For instance, Japanese Patent Application No. 2003-267471 and Japanese Patent Application No. 2000-140069 each disclose a covering bag, which is obtained by forming a film with excellent impact resistance into a bag shape to protect a freezing bag, and a metallic container for accommodating the covering bag covering the freezing bag. The covering bag and the metallic container are designed for consistently protecting and storing the freezing bag throughout the above-described process of freezing and thawing the cells in the freezing bag. At the time of freezing, however, part of the freezing bag may be rapidly cooled, such that cells in the freezing bag may be frozen non-uniformly. At the time of thawing, on the other hand, the freezing bag may fail to be appropriately (i.e., sufficiently) warmed up, and insufficient thawing of the biological tissue may occur, resulting in a lowered recovery rate.

SUMMARY OF INVENTION

The container of this application can help protect a freezing bag filled with biological tissue and can provide an enhanced recovery rate of the biological tissue through appropriate freezing and thawing (e.g., can provide an improved container for addressing some of the background issues discussed above).

The present inventor made extensive and intensive researches for helping to address one or more of the above-mentioned problems. For enhancing recovery rate of biological tissue put to freezing and thawing, the inventor has found it is necessary to restrain excessively rapid freezing the biological tissue and to achieve comparatively rapid warming at the time of thawing. As a result of further research, the present inventor has found that by providing an air gap between a freezing bag and an inner surface of a container and providing an opening for securing a flow path of hot water, it is possible to provide a freezing bag container by which a series of operations of cooling, freezing, preservation, warming, thawing and the like can be consistently performed in a state wherein a freezing bag is contained and protected in the container and by which a good recovery rate is achieved.

The container disclosed in this application relates to the following.

(1) A container, which is substantially rectangular parallelepiped-shaped, for containing a freezing bag filled with biological tissue and for cooling and warming the freezing bag, the container including: at least one opening formed in a side surface of the container; and at least two ridges formed at an inner surface of the container to form an air gap between the inner surface and the freezing bag.

(2) The container as described in the above paragraph (1), wherein the opening is provided in each of two opposed side surfaces of the container, to form a flow path between the opening on one side and the opening on the other side.

(3) The container as described in the above paragraph (2), wherein the ridges are formed at an inner surface or surfaces of an upper surface and/or a lower surface of a main body of the container in such a manner as to extend in parallel to a flow path direction of the flow path.

(4) The container as described in any one of the above paragraphs (1) to (3), wherein a section of the ridge has an arcuate shape.

(5) The container as described in any one of the above paragraphs (1) to (4), wherein the opening has such a shape as to be connectable to a pipe.

(6) The container as described in any one of the above paragraphs (1) to (5), further including a protective bag for containing and protecting the freezing bag, wherein the protective bag has ridges formed with engaging grooves for engagement with the at least two ridges of the container.

(7) The container as described in any one of the above paragraphs (1) to (6), wherein the opening has an openable and closable structure.

The container helps allow cooling and heating of the freezing bag to be performed consistently and appropriately. By providing an air gap between the freezing bag and the container, thermal conductivity between the freezing bag and the container may be lowered and rapid cooling of the freezing bag can be prevented at the time of freezing.

Therefore, biological tissue in the freezing bag is frozen relatively uniformly, so that recovery rate is enhanced. On the other hand, the container is provided with an opening, whereby hot water can be introduced as appropriate. At the time of thawing, hot water flows into the air gap, whereby the area of contact between the hot water and the freezing bag is increased, and the freezing bag is warmed up appropriately. Therefore, re-freezing of the biological tissue in the freezing bag does not occur, so that recovery rate is enhanced. A series of operations of cooling, freezing, preservation, warming, thawing and the like can be carried out consistently while protecting the freezing bag.

In another aspect, a container for containing a freezing bag filled with biological tissue is disclosed. The container includes: a main body comprising an interior, an upper surface, a lower surface, a first side surface and a second side surface positioned opposite the first side surface; a first opening penetrating through the first side surface; and a second opening penetrating through the second side surface, the second opening being positioned opposite the first opening so that a flow path is formed within the container from the first opening to the second opening. The container also includes two upper ridges spaced apart from one another on the upper surface of the container. The two upper ridges protrude from the upper surface towards the interior of the container. The two upper ridges create a first air gap between the upper surface of the container, the outer surface of the freezing bag and the two upper ridges when the freezing bag is within the interior of the container. The container has two lower ridges spaced apart from one another on the lower surface of the container. The two lower ridges protrude from the lower surface towards the interior of the container. The two lower ridges create a second air gap between the upper surface of the container, the outer surface of the freezing bag and the two upper ridges when the freezing bag is within the interior of the container.

In yet another aspect, the disclosed container includes a main body comprising an interior, an upper surface, a lower surface, a first side surface and a second side surface positioned opposite the first side surface. The container includes a freezing bag within the interior of the main body of the container. The freezing bag has an interior filled with biological tissue and possesses an outer surface. The container includes a first opening penetrating through the first side surface and a second opening penetrating through the second side surface. The second opening is positioned opposite the first opening so that a flow path is formed within the container from the first opening to the second opening. The container includes two lower ridges spaced apart from one another on the lower surface of the container. The two lower ridges protrude from the lower surface towards the interior of the container. The two lower ridges contact the outer surface of the freezing bag at spaced apart contact points to support the freezing bag within the interior of the main body. An air gap is defined between the lower surface of the container, the outer surface of the freezing bag between the two spaced apart contact points, and the two lower ridges spaced apart from one another on the lower surface of the container.

DETAILED DESCRIPTION

Set forth below with reference to the accompanying drawings is a detailed description of embodiments of a container representing examples of the inventive container disclosed here. Note that the sizes of members in the drawings are appropriately exaggerated, and, therefore, may not be the actual proportions or sizes.

Figure 1:
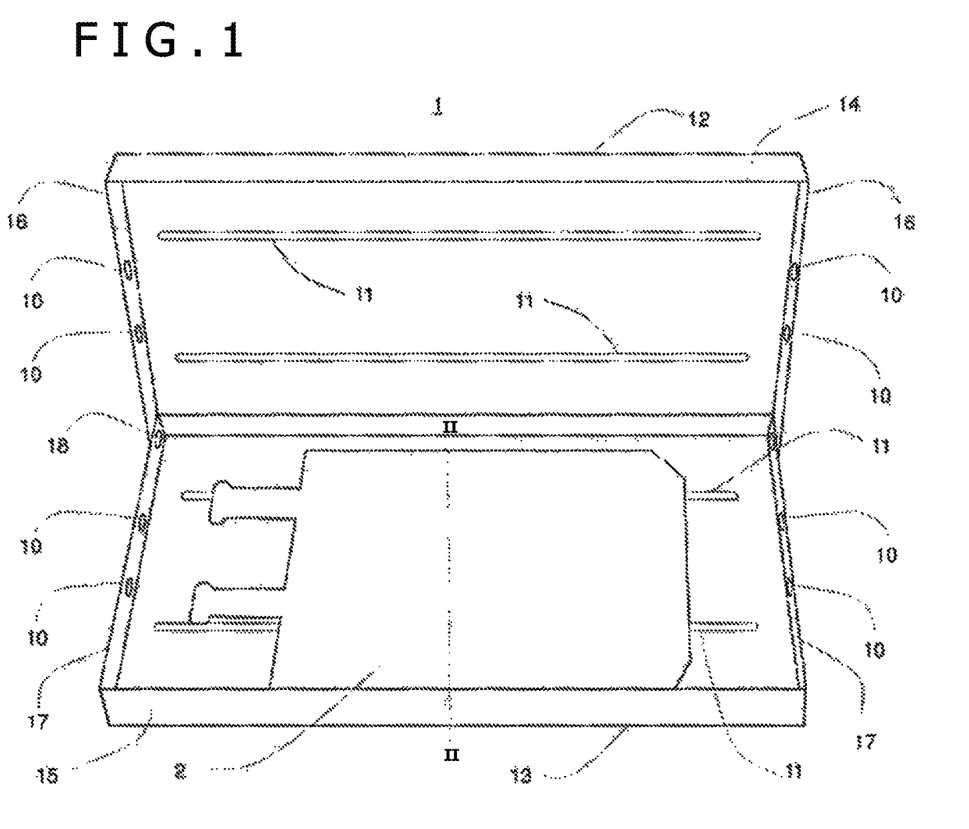
FIG. 1 is a perspective view of an embodiment of a container.

FIG. 1 is a perspective view of a container according to one embodiment. The container 1 has a substantially rectangular parallelepiped shape (e.g., a rectangular box, a rectangular cuboid or a rectangular prism) such as to be able to (i.e., configured to) accommodate a freezing bag 2 within the container 1. The container 1 has an upper portion 14 and a lower portion 15. The container 1 can be opened and closed while accommodating the freezing bag 2 within the interior of the container 1 by rotating the upper portion 14 relative to the lower portion 15 about a hinge 18. The container 1 has ridges 11 at an inner surface of an upper surface 12 of the upper portion 14 and at an inner surface of a lower surface 13 of the lower portion 15. Two ridges 11 are formed on the inner surface of each of the upper surface 12 and the lower surface 13.

The freezing bag 2 is supported by the two ridges 11 formed on the inner surface of the lower surface 13 (i.e., the outer surface of the freezing bag 2 contacts the two ridges 11 at spaced apart contact points to be supported by the two ridges 11). The container 1 has openings 10 in opposing side surfaces (i.e., lateral sides opposite to one another as shown in FIG. 1) of the container 1. More specifically, two openings 10 are formed in the opposing side surfaces 16 of the upper portion 14 and two openings are formed in the opposing side surfaces 17 of the lower portions 15. The openings 10 in the upper portion 14 and the openings 10 in the lower portion 15 are positioned to correspond to each other (i.e., the openings 10 in the upper portion 14 are aligned with the openings 10 in the lower portion 15 as shown in FIG. 1). The openings 10 penetrate the side surfaces 16 of the upper portion 14 and the side surfaces 17 of the lower portion 15 when the container 1 is closed (i.e., when the container 1 is in the closed state).

The material constituting the container 1 is not particularly restricted, so long as the container 1 material has excellent durability and thermal conductivity. The container 1 material is preferably a rigid metallic material such as, for example, iron, stainless steel, aluminum, copper or brass. Utilizing this type of container 1 material helps protect the freezing bag 2 contained in the container 1, and helps transfer heat applied to the container 1 to the freezing bag 2. The shape of the container 1 is not particularly restricted, so long as the container 1 can be hermetically sealed with the freezing bag 2 contained within the container 1. The container 1 shape is preferably an elongated and flat shape such that the inner surfaces of the container 1 can surround the freezing bag 2, for example. An elongated and relatively flatly-shaped container 1 can help efficiently transfer the heat applied to the container 1 to the freezing bag 2, while the freezing bag 2 is kept in a fixed position (i.e., unmoved)

within the container 1. The container 1 preferably has a substantially rectangular parallelepiped shape such that a plurality (multiplicity) of the containers 1 can be transported, stored and alignedly contained in a stable state in liquid nitrogen. The opening/closing structure of the container 1 is not specifically restricted, so long as the freezing bag 2 can be put into (i.e., placed within the interior of the container 1) and taken out of the container 1 (i.e., removed from the interior of the container 1).

The dimensions of the container 1 are not particularly restricted, so long as the freezing bag 2 can be contained in the container 1. For example, the length can be 50 to 500 mm, 80 to 300 mm, or 100 to 200 mm, the width can be 30 to 400 mm, 50 to 200 mm, or 80 to 150 mm, and the height can be 5 to 30 mm, 8 to 20 mm, or 10 to 15 mm.

The openings 10 are not specifically restricted to the configuration illustrated in FIG. 1, so long as fluid can move between the outside and the inside of the container 1. For example, the openings 10 may be provided in the upper surface 12, the lower surface 13, the side surfaces and the like of the container 1. The number of the openings 10 is not particularly restricted, so long as fluid can move between the outside and the inside of the container. For example, the number of openings can be one, two, three, four, five, six, seven, eight, nine, ten or more. The size of the openings 10 is not particularly restricted, so long as durability and thermal conductivity of the container 1 can be maintained. For example, the openings 10 may be relatively small or relatively large based on whether more or fewer openings 10 are provided, whereby the durability and thermal conductivity of the container 1 can be maintained.

The openings 10 can be provided respectively in two opposed side surfaces (i.e., two side surfaces position directly opposite one another) of the container 1, for example. This configuration helps ensure that a flow path can be formed between the opening on one side and the opening on the opposite side, so that fluid in the outside of the container 1 enters the inside of the container 1 via the opening on one side and moves rectilinearly toward the opening on the opposite side, whereby discharge of the fluid can be performed smoothly.

The ridges 11 are not specifically restricted, so long as they can form an air gap between at least two spaced apart ridges 11, the freezing bag 2 and the container 1. The ridges 11 may be formed on inner surfaces of the container 1, for example, the inner surface of the lower surface 13, the inner surface of the upper surface 12, or the inner surfaces of the side surfaces of the container 1. The number of the ridges 11 is not particularly restricted, so long as the freezing bag 2 can be appropriately supported and an air gap can be formed between two ridges 11, the freezing bag 2 and the container 1. For example, the number of the ridges 11 may be two, three, four, five, six, seven, eight, nine, ten or more. In an embodiment, two or more ridges 11 are provided on the inner surface of both the lower surface 13 and the upper surface 12. This configuration helps ensure that the freezing bag 2 is supported appropriately, an air gap is formed both between the upper surface (outer surface) of the freezing bag 2 and the upper surface 12 of the container 1 (i.e., defining a first air gap) and between the lower surface of the freezing bag 2 and the lower surface 13 of the container 1 (i.e., defining a second air gap), and fluid flowing into the container 1 moves to both the upper surface and the lower surface of the freezing bag 2, so that the freezing bag 2 can be appropriately warmed by hot water.

The dimensions of the ridge 11 are not particularly restricted, so long as the freezing bag 2 can be appropriately supported. For example, the length of the ridge 11 can be 10 to 450 mm, 100 to 300 mm, 100 to 200 mm, 60 to 100 mm, 20 to 45 mm, or 10 to 30 mm, and the height of the ridge 11 can be 0.5 to 10 mm or 1 to 5 mm. The shape of the ridge 11 is not specifically restricted, so long as the freezing bag 2 can be appropriately supported and an air gap can be formed between two ridges 11, the container 1 and the freezing bag 2. Typically, the ridge 11 is a protrusion extending in a longitudinal direction and crossing the whole or part of one surface of the container 1. The extending direction of the ridge 11 is not specifically restricted. For example, when a flow path is formed between the opening on one side and the opening on the opposite side as described above, the extending direction of the ridge 11 may be parallel to the flow path, whereby fluid can be guided along the flow path direction without hindering the flow of the fluid.

Figure 2:
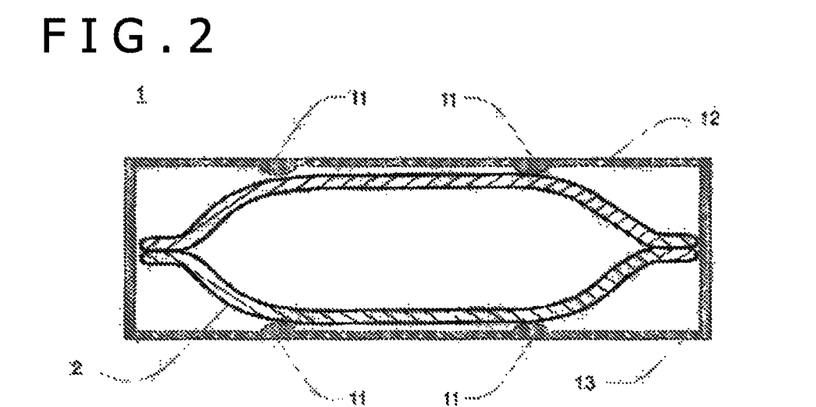
FIG. 2 is a sectional view taken along line II-II of FIG. 1.

FIG. 2 is a sectional view taken along line II-II of FIG. 1. Two ridges 11 are formed on the inner surface of the upper surface 12 and two ridges 11 are on the inner surface of the lower surface 13 of the container 1. The freezing bag 2 is supported by the two ridges 11 at the upper surface 12 of the container 1 and the two ridges 11 at the lower surface 13 of the container 1 (i.e., the ridges 11 are configured to support the freezing bag 2). The ridges 11 project from the inner surface of the container 1 (i.e., toward the interior of the container 1) to create an air gap between the two ridges 11, the outer surface of the freezing bag 2 and the inner surface of the container 1.

The material constituting the ridges 11 is not specifically restricted, so long as the ridge 11 material possesses relatively excellent thermal conductivity. The ridge 11 material is preferably a rigid metallic material such as, for example, iron, stainless steel, aluminum, copper or brass. Heat applied to the container 1 can thus be efficiently transferred to the freezing bag 2. The sectional shape of the ridge 11 is not specifically restricted, so long as the freezing bag 2 can be supported. For example, the sectional shape of the ridge 11 (i.e., the cross-sectional shape) may be semicircular, arcuate, triangular, rectangular, polygonal or the like. Preferably, the sectional shape is a rounded shape. A rounded shape helps prevent the ridges 11 from inadvertently damaging the freezing bag 2. The ridges 11 may be molded integrally with the container 1, or may be molded as separate bodies from the container 1 and then attached to the container 1.

Figure 3:
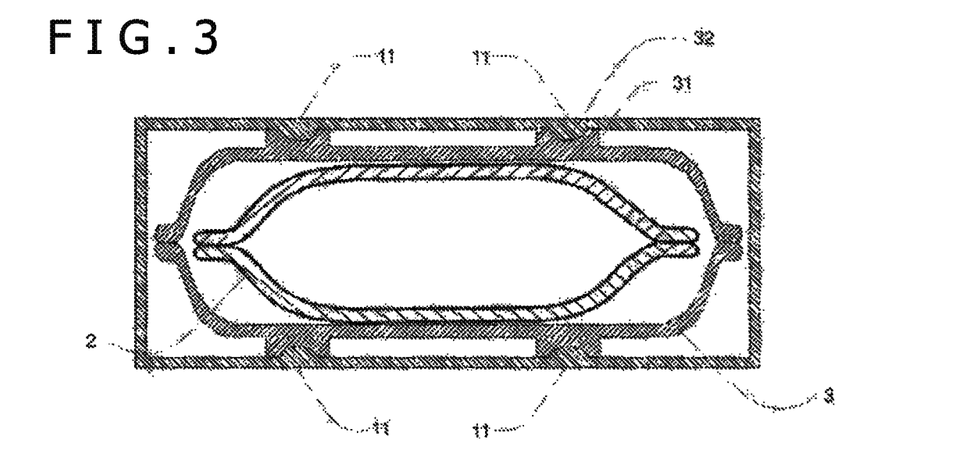
FIG. 3 is a sectional view of a protective bag for protecting a freezing bag.

FIG. 3 is a sectional view of a protective bag 3 for protecting the freezing bag 2. The protective bag 3 is for containing and protecting the freezing bag 2. The protective bag 3 has an opening for putting the freezing bag 2 in and out (i.e., to allow the freezing bag 2 to be placed into the protective bag 3 and to remove the freezing bag 2 from the protective bag 3). The protective bag 3 has ridges 31, which are formed with engaging grooves 32. The engaging grooves 32 engage with the ridges 11 of the container 1 (i.e., the ridges 11 of the container 1 can be positioned on or seat within the engaging grooves 32 of the protective bag 3), whereby the protective bag 3 can be accurately positioned inside the container 1. The ridges 31 have a height large enough to form the engaging grooves 32 in the ridges 31. When the ridges 31 of the protective bag 3 are engaged with the ridges 11 of the container 1, heat applied to the container 1 can be slowly transmitted to the freezing bag 2 through the ridges 11 and the ridges 31.

The material constituting the protective bag 3 is preferably a flexible resin material excellent in flexibility or pliability. Using a flexible resin facilitates the operation of moving the freezing bag 2 into the protective bag 3 and removing the freezing bag 2 from the protective bag 3. Such a resin material is not specifically restricted, and examples include polyolefins such as polyethylene, polypropylene, polybutadiene, ethylene-vinyl acetate copolymer, etc., polyesters such as polyethylene terephthalate, polybutylene terephthalate, etc., flexible polyvinyl chloride, polyvinylidene chloride, silicone, polyurethane, styrene-butadiene copolymer, various thermoplastic elastomers such as polyamide elastomers, polyester elastomers, etc., and their arbitrary combinations (blend resins, polymer alloys, laminates, etc.). Polypropylene-based flexible resins are particularly preferred, from the viewpoints of sealing properties, heat resistance, water resistance, flexibility, and processibility. The material of the protective bag 3 is additionally preferably a transparent resin material to allow visual observation of the biological tissue in the freezing bag 2 and to allow the position of the freezing bag 2 to be visually confirmed.

Figure 4:
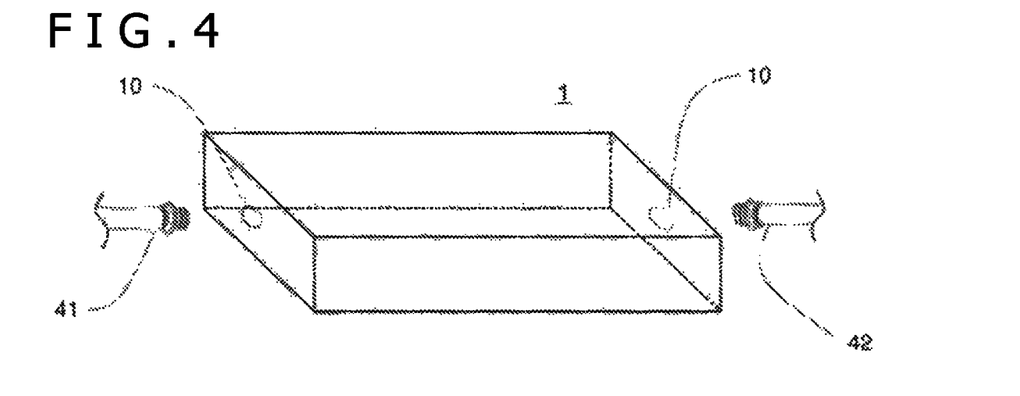
FIG. 4 is a perspective view illustrating an embodiment of an opening.

FIG. 4 is a perspective view indicating another embodiment of the container 1. In the container 1 embodiment shown in FIG. 4, one opening 10 is provided in each of two opposing side surfaces of the container 1, and a rectilinear flow path is formed between the opening on one side and the opening on the other side (i.e., the opposite side). A hot water pipe 41 and a drain pipe 42 can be attached to the openings 10. At the time of thawing, hot water can be delivered through the hot water pipe 41 into the container 1 to warm the freezing bag 2 in the container 1. The hot water (which has been lowered in temperature through heat exchange) can be drained through the drain pipe 42. In addition, since the hot water delivered through the hot water pipe 41 passes the air gaps formed between the freezing bag 2 and the container 1 as described above, the freezing bag 2 in the container 1 can be relatively rapidly warmed up. After the freezing bag 2 has thawed, the hot water pipe 41 and the drain pipe 42 can be detached from the openings 10. The openings 10 are each formed with, for example, a screw engagement portion, a fitting portion, an engagement portion or the like so that a pipe (for example, the hot water pipe 41, the drain pipe 42, an air feed pipe, an exhaust pipe or the like) can be attached to each of the openings 10.

Figure 5:
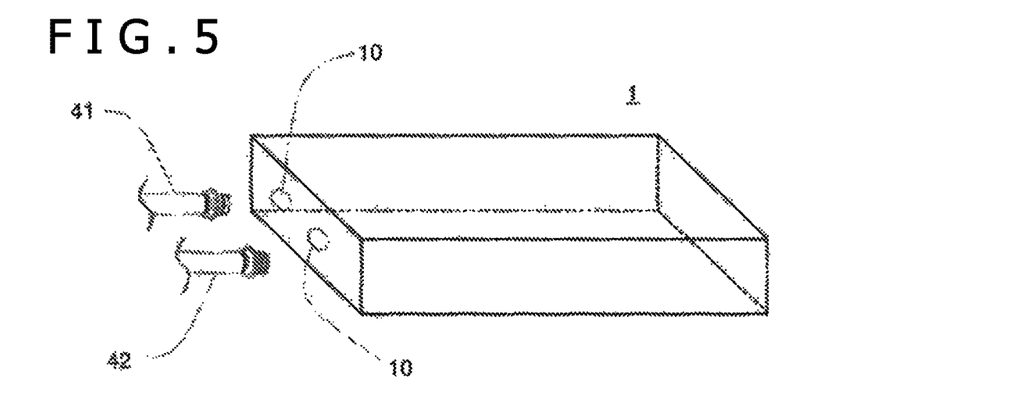
FIG. 5 is a perspective view illustrating an embodiment of the opening.

FIG. 5 is a perspective view illustrating another embodiment of the container 1. In the container 1 embodiment shown in FIG. 5, two openings 10 are provided in a side surface (i.e., on the same side surface) of the container 1. The hot water pipe 41 and the drain pipe 42 can be attached to the openings 10. At the time of thawing, hot water can be delivered through the hot water pipe 41 into the container 1 to warm the freezing bag 2 in the container 1. The hot water (which has been lowered in temperature through heat exchange) can be drained through the drain pipe 42.

Figure 6:
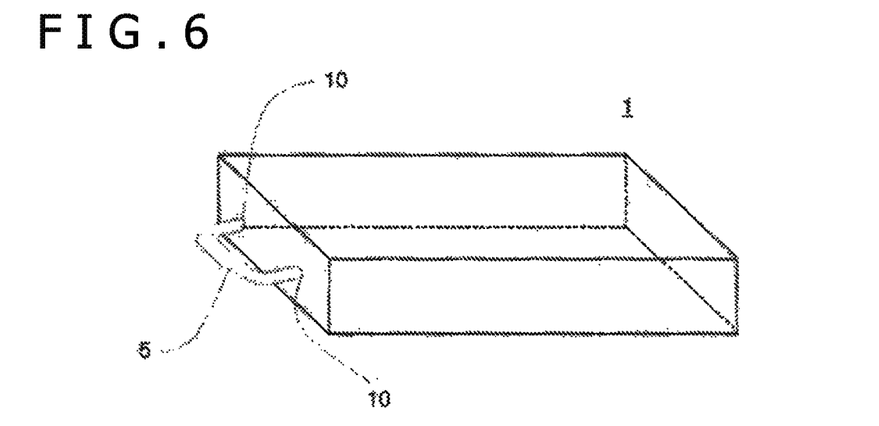
FIG. 6 is a perspective view illustrating an embodiment of the opening.

FIG. 6 is a perspective view illustrating another embodiment of the container 1. In the container 1 embodiment shown in FIG. 6, two openings 10 are provided in a side surface (i.e., the same side surface) of the container 1. A handle 5 can be attached to the openings 10. This configuration allowing a handle 5 to be attached to the openings 10 simplifies or facilitates handling of the container 1. In addition, the openings 10 can be closed by attaching the handle 5 to the openings 10. Closing the openings 10 in this manner helps ensure that, for example, when the container 1 is immersed in liquid nitrogen and then stored, foreign matter is prevented from penetrating into the container 1 to damage the freezing bag 2.

At the time of thawing, by detaching the handle 5 from the openings 10 to open the openings 10, then attaching the pipe described above (the hot water pipe 41) and feeding in hot water, the freezing bag 2 in the container 1 can be rapidly warmed up. The openings 10 are thus closed at the time of cryopreservation and the openings 10 are opened at the time of thawing, whereby a series of operations of cooling, freezing, preservation, warming, thawing and the like can be carried out efficiently and consistently. Therefore, the openings 10 of the present invention preferably have an openable and closable structure. Such an openable and closable structure can be realized by use of various known processing methods, members and assembling methods, and persons skilled in the art can appropriately determine a suitable openable and closable structure.

Figure 7:
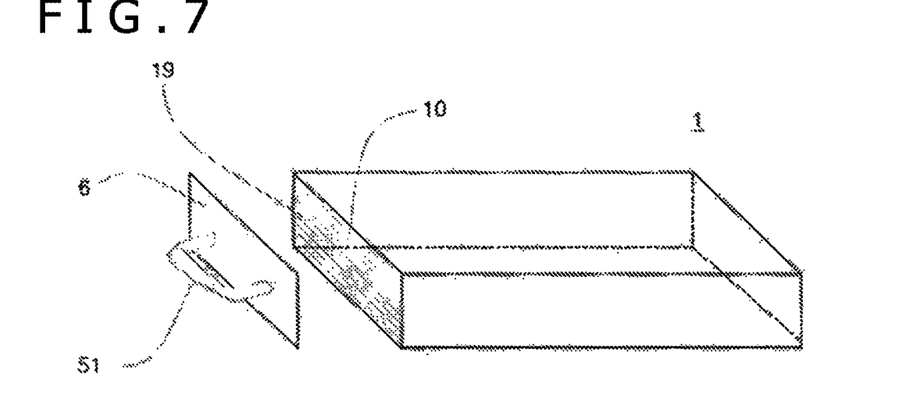
FIG. 7 is a perspective view illustrating an embodiment of the opening.

FIG. 7 is a perspective view illustrating another embodiment of a container 1. In the container 1 shown in FIG. 7, one opening 10 is provided in a side surface of the container 1. A grid-like structure body 19 is attached to the opening 10, such that the freezing bag 2 in the container 1 would not inadvertently fly out. A lid 6 can be detachably attached to the opening 10. The lid 6 is fitted with a handle 51. At the time of freezing, the lid 6 is attached to the opening 10 to close the opening 10, whereby the freezing bag 2 in the container 1 can be sealed. At the time of thawing, the lid 6 is detached from the opening 10 to open the opening 10, whereby hot water is allowed to flow into the container 1.

The container of this application has such a configuration that thermal conductivity between the freezing bag and the container can be reduced at the time of freezing and the area of contact between the freezing bag and hot water can be increased at the time of thawing. Therefore, excessively rapid freezing can be restrained, and comparatively rapid warming can be achieved when thawing the freezing bag. The container helps enable operations of cooling, freezing, preservation, warming and thawing to be carried out consistently while the freezing bag is accommodated in and protected by the container.

While the embodiments illustrated in the drawings have been described above, the disclosed container is not restricted to the embodiments.

Each component can be replaced by an arbitrary one capable of exhibiting an equivalent function or an arbitrary component can be added.

For instance, the container 1 is not restricted to be formed using a rigid metallic material as described above. For example, the upper surface 12, the lower surface 13, the side surfaces 16 and 17, the openings 10, the ridges 11, the lid 6 and the like of the container 1 can be manufactured using respectively different materials. While the ridges 31 and the engaging grooves 32 have been described to be provided in the protective bag 3, they may be provided in the freezing bag 2, for example. The structure body 19 attached to the opening 10 has been described to be a grid-like body, but the structure body 19 may be a mesh-like body. Furthermore, the ridges 11 are not limited to being longitudinally extending protrusions as described in the above embodiments. For example, the ridges 11 may each be a longitudinally extending protrusion formed by arranging a plurality of protrusions having such a shape as a conical shape, a hemispheric shape, or a rectangular shape.

The detailed description above describes a freezing bag container. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A container assembly comprising:
    a main body comprising an interior, an upper surface, a lower surface, a first side surface and a second side surface positioned opposite the first side surface, the main body being a hollow rectangular prism;
    a freezing bag within the interior of the main body of the container, the freezing bag comprising an interior filled with biological tissue, the freezing bag possessing an outer surface;
    a first opening penetrating through the first side surface;
    a second opening penetrating through the second side surface so that a flow path is formed within the container from the first opening to the second opening;
    two lower ridges spaced apart from one another on the lower surface of the container, the two lower ridges protruding from the lower surface towards the interior of the container to support the freezing bag within the interior of the main body; and
    an air gap defined between the two lower ridges spaced apart from one another on the lower surface of the container.

2. The container assembly according to claim 1, further comprising:
    two upper ridges spaced apart from one another on the upper surface of the container, the two upper ridges protruding from the upper surface towards the interior of the container, and
    a second air gap between the upper surface of the container, the outer surface of the freezing bag and the two upper ridges.

3. The container assembly according to claim 1, further comprising:
    a protective bag in the interior of the main body, the protective bag comprising an interior, and
    the freezing bag being within the interior of the protective bag.

4. The container assembly according to claim 3, wherein the protective bag comprises at least two ridges protruding toward the two lower ridges of the container, the at least two ridges each comprising an engaging groove, and the two lower ridges of the container being positioned within the engaging grooves of the protective bag to hold the protective bag within the container.

5. The container assembly according to claim 1, wherein the outer surface of the freezing bag directly contacts both of the lower ridges.

6. A container for containing a freezing bag filled with biological tissue and for cooling and warming the freezing bag, the freezing bag possessing an outer surface, the container comprising:
    a main body comprising an inner surface forming an interior of the main body, a first side surface and a second side surface positioned opposite the first side surface, the main body being rectangular parallelepiped shaped, and the interior of the main body being configured to receive the freezing bag filled with the biological tissue;
    a first opening provided in the first side surface, the first opening penetrating through the first side surface;
    a second opening provided in the second side surface, the second opening penetrating through the second side surface;
    the second opening being opposite the first opening to form a flow path between the first opening on the first side surface and the second opening on the second side surface; and
    at least two ridges spaced apart from one another on the inner surface of the container.

7. The container according to claim 6, wherein
    the inner surface of the main body comprising an upper surface and a lower surface opposite the upper surface, the upper and lower surfaces being orthogonal to the first and second side surfaces, and
    the at least two ridges are formed on at least one of the upper surface and the lower surface of the inner surface of the main body of the container such that the at least two ridges extend in parallel to a flow path direction of the flow path.

8. The container according to claim 6, wherein the at least two ridges each comprise a section that has an arcuate shape.

9. The container according to claim 6, wherein the first opening is shaped to be connectable to a pipe.

10. The container according to claim 6, wherein the first opening has an openable and closable structure.

11. A container for containing a freezing bag filled with biological tissue, the freezing bag possessing an outer surface, the container comprising:
    a main body comprising an interior for receiving the freezing bag filled with the biological tissue, an upper surface, a lower surface, a first side surface upstanding from the lower surface and a second side surface positioned opposite the first side surface and upstanding from the lower surface;
    a first opening penetrating through the first side surface;
    a second opening penetrating through the second side surface so that a flow path is formed within the container from the first opening to the second opening;
    two upper ridges spaced apart from one another on the upper surface of the container, the two upper ridges protruding from the upper surface towards the interior of the container, the two upper ridges configured to create a first air gap between the upper surface of the container, the outer surface of the freezing bag and the two upper ridges when the freezing bag is within the interior of the container and the outer surface of the freezing bag directly contacts the two upper ridges;
    two lower ridges spaced apart from one another on the lower surface of the container, the two lower ridges protruding from the lower surface towards the interior of the container, the two lower ridges configured to create a second air gap between the upper surface of the container, the outer surface of the freezing bag and the two upper ridges when the freezing bag is within the interior of the container and the outer surface of the freezing bag directly contacts the two lower ridges; and
    the two upper ridges and the two lower ridges extending parallel to the flow path formed between the first opening and the second opening.

12. The container according to claim 11, wherein the main body is a hollow rectangular prism.

13. The container according to claim 11, wherein
    the first and second openings are sealable when the freezing bag is placed within the container so that the container with the freezing bag is immersable in liquid nitrogen to cool the biological tissue in the freezing bag; and
    the first opening is connectable to an inlet pipe permitting fluid that is heated to be introduced into the interior of the container when the freezing bag is positioned in the interior of the container to thaw the biological tissue in the freezing bag and the second opening is connectable to a drain pipe permitting the fluid introduced into the interior of the container to be drained out of the interior of the container.

14. The container according to claim 11, wherein the main body comprises an upper portion which includes the upper surface and a lower portion which includes the lower surface, the upper portion being connected to the lower portion by a hinge such that the upper portion is rotatable relative to the lower portion to open the container.

15. The container according to claim 14, wherein the upper portion comprises the first and second openings, and the lower portion comprises a third opening on the first side surface of the container and a fourth opening on the second side surface opposite the first side surface of the container.

* * * * *